United States Patent
Grundei et al.

(10) Patent No.: US 6,245,110 B1
(45) Date of Patent: Jun. 12, 2001

(54) SHANKLESS KNEE JOINT ENDOPROSTHESIS

(75) Inventors: Hans Grundei, Lübeck (DE); Wolfram Thomas, Rome (IT)

(73) Assignee: ESKA Implants GmbH & Co., Lubeck (DE)

( * ) Notice: Subject to any disclaimer, the term of this patent is extended or adjusted under 35 U.S.C. 154(b) by 0 days.

(21) Appl. No.: 09/460,606

(22) Filed: Dec. 14, 1999

Related U.S. Application Data

(63) Continuation of application No. PCT/EP98/03857, filed on Jun. 24, 1998.

(30) Foreign Application Priority Data

| Jul. 4, 1997 | (DE) | 197 28 636 |
| Oct. 16, 1997 | (DE) | 197 45 632 |

(51) Int. Cl.[7] .................................... A61F 2/38
(52) U.S. Cl. .................. 623/20.31; 623/20.32; 623/20.35
(58) Field of Search ............... 623/20.31–20.33, 623/20.16, 20.11–20.14, 20.17, 20.21, 20.35

(56) References Cited

U.S. PATENT DOCUMENTS

| 4,502,161 | | 3/1985 | Wall . | |
| 4,911,720 | * | 3/1990 | Collier | 623/20.11 |
| 4,963,152 | * | 10/1990 | Hofmann et al. | 623/20.32 |
| 5,207,711 | | 5/1993 | Caspari et al. . | |
| 5,282,867 | | 2/1994 | Mikhail . | |
| 5,344,460 | * | 9/1994 | Turanyi et al. | 623/20.31 |
| 5,344,461 | * | 9/1994 | Phlipot | 630/20.11 |
| 5,522,902 | | 6/1996 | Yuan et al. . | |
| 5,928,286 | * | 7/1999 | Ashby et al. | 623/20.32 |
| 6,162,254 | * | 12/2000 | Timoteo | 623/20.33 |

FOREIGN PATENT DOCUMENTS 2007 980    5/1979  (GB) .

* cited by examiner

*Primary Examiner*—David H. Willse
*Assistant Examiner*—Suzette J. Jackson
(74) *Attorney, Agent, or Firm*—Akin, Gump, Strauss, Hauer & Feld, L.L.P.

(57) ABSTRACT

A knee joint endoprosthesis has an element for the femur (2) which is substantially U-shaped when seen from a medial to a lateral angle, one horizontal, two diagonal and two vertical support surfaces facing the femur for accommodation on the resected femur bone, which is fitted with two runners (24, 25), and an element for the tibia (1) having two slide tracks (4, 5) on which the runners for the femur element can roll, and optionally slide, and a horizontal support surface (6) facing the tibia for accommodation on the resected tibia. The femur element (20) and tibia element (1) are configured without any shanks. At least both diagonal support surfaces of the femur element (2) and the horizontal support surface (6) of the tibia element (20) are fitted with an open-mesh, three-dimensional spatial network structure (7) which is an integral component of the base structures (8, 8') of the femur element (20) and the tibia element (1). Two latches (21, 22) angled toward the femur and provided with at least one respective through hole (23) are medially and laterally formed on the femur element (20), whereby a bone screw (26) can be inserted therein; and two latches (11,12) angled toward the tibia and provided with at least one respective through hole (18) are formed on the tibia element, whereby a bone screw (14) can be inserted therein.

9 Claims, 5 Drawing Sheets

SHANKLESS KNEE JOINT ENDOPROSTHESIS

CROSS REFERENCE TO RELATED APPLICATION

This application is a continuation of International Application PCT/EP98/03857, filed Jun. 24, 1998, the disclosure of which is incorporated herein by reference.

BACKGROUND OF THE INVENTION

The present invention relates to a knee joint endoprosthesis having a femur element and a tibia element.

Such systems are known, for example, from DE-A 41 41 757. There, the femur element, viewed from medial to lateral, has an essentially U-shape, wherein one horizontal, two diagonal and two vertical joint surfaces pointing toward the femur are provided for installation on a resected femur bone. The femur element is provided with two runners which reproduce the natural condyles and condyle rollers.

The tibia element of known systems usually has two sliding tracks, on which the runners of the femur element can execute a rolling away motion and, optionally (depending upon the type of endoprosthesis), sliding movements. The tibia element has a horizontal support surface pointing toward the tibia for supporting the resected tibia.

The tibia element as well as the femur element of known systems respectively have a conical pin, which is insertable into a conical taper socket in a respective shank element of the modular system. Between pin and socket a conical friction (clamping) connection can be produced, which should ensure a durable connection between femur element and femur shank element or tibia element and tibia shank element.

The shanks of modular systems are implanted either by means of a bone cement, for example PMMA, into the marrow space of the respective tubular bone, or without cement, whereby the shank element is then provided with a special surface into which and through which bone material can grow for durable secondary fixation of the implant (see, for example, German Patent DE-C-195 435 30).

The following problems are associated with the known systems:

The shanks (generally made of metal), which are installed in the marrow space of the respective tubular bone, have a completely different elasticity modulus than the bone material (spongiosa) surrounding the shank. This often leads (especially with older persons, whose bones are diseased with osteoporosis) to fatigue fractures above the shank end in the marrow space precisely because of the different elasticity moduli.

The second problem concerns the natural valgus angle, which lies in the range of 7.5° with most people. With the artificial endoprosthesis systems, however, only valgus angles of at most 5° have been producible up until now, and to be sure owing to the previously mentioned conical clamping usually used between the shank element and the femur element or tibia element, since the desired conical clamping no longer occurs with an angle >5°.

Moreover, finding sufficient hold for a new shank endoprosthesis, so that this can be implanted sufficiently firmly, is problematic with the known shank endoprostheses in the event that a revision intervention should become necessary. This is especially critical in younger patients since, according to previous experience, implanted endoprostheses have a limited lifetime of 10 to 15 years, assuming that an unforeseen revision intervention is not necessary before this. With younger patients, it is then in any case necessary to replace the originally implanted endoprosthesis with a new one. This is not always possible, without further measures, for the reasons mentioned.

SUMMARY OF THE INVENTION

Against this background, it is now the object of the present invention to provide a completely new type of knee joint endoprosthesis, in which the problems of known endoprostheses with respect to different elasticity moduli of the implant material and the surrounding bone material do not arise, and in which the restriction with respect to reproducibility of the valgus angle does not exist.

This object is accomplished with a knee joint endoprosthesis with the features mentioned at the beginning by the combination of the features presented below:

1. The femur element and the tibia element are constructed shanklessly. This means that neither the femur element nor the tibia element is to be connected with a modular shank element. The restriction of the valgus angle to a maximum of 5° is thereby absent, since no conical clamp connection must be produced between a respective shank element and the tibia or femur element. The problem in respect to the abutting different elasticity moduli in the marrow space of the tibia or femur also disappears, since no shank is inserted into the marrow space. Basically, the femur element therefore grips around the resected femur end without a shank penetrating into the marrow cavity of the femur. The tibia element, in contrast, lies on the resected bearing surface of the tibia, without it having the known shank which would have to be coupled with it through a conical clamp connection.

With respect to the valgus position, as well as with respect to avoiding the different elasticity moduli impinging upon each other, the shanklessness feature mentioned accomplishes the object previously mentioned. The long term in situ stability of an endoprosthesis constructed in this manner is attained through the following feature.

2. At least the horizontal and the two diagonal joint surfaces of the femur element and the horizontal support surface of the tibia element are provided with an open-mesh, three-dimensional spatial network structure, which is an integral component of the base structure of the femur element and the tibia element. The latter should be stressed in particular, since the three-dimensional spatial network structure is the only component of the endoprosthesis which provides for a stable secondary fixation of the femur element and the tibia element in situ. Any sintered-on metal network would not do the stresses justice. It is contemplated to use of a spatial network structure as disclosed, for example, in German patents DE-C-41 06 971 or DE-C-195 43 530, where so-called tripods are produced as an integral component of the base structure of the femur element and the tibia element by an investment casting process.

In order that the bone material be integrated into the open-mesh spatial network structure in the shortest time possible, the two features reproduced below are provided:

3. Medially and laterally, two latches angled toward the femur are formed on the femur element with respectively at least one through hole formed therein, into which respectively a bone screw can be inserted, and 4. Medially and laterally, two latches angled toward the tibia are formed on the tibia element with respectively at least one through hole formed therein, into which respectively a bone screw can be inserted.

The angling of the mentioned latches is of particular importance in the present case. Namely, by screwing in the respective bone screws, which are inserted through the mentioned through holes in the latches, a diagonal bracing of the femur element or the tibia element is hereby attained, wherein the screws can extend through the spongiosa tissue up to the opposite cortical bone and further beyond, so that they can even penetrate the opposite cortical bone. By the diagonal bracing respective compressive forces with horizontal and vertical components are exerted on the interface between the spatial network structure and the resected bone. The bone material, which comes into contact with the spatial network structure, is hereby stimulated to grow, so that the integration in the open-mesh proceeds in an accelerated manner. The screws screwed into the bones therefore have a smaller effect in respect to a stable secondary fixation, but rather much more in respect to a primary fixation and in relation to the exertion of diagonally acting compressive forces. After complete integration of bone material into the spatial network structure, the bone screws cease to exercise any function at all. Theoretically, they can be removed at this time, which is not conducted in practice, however, as this would mean a new operation.

With the intended secondary fixation as described, an osteosynthesis between the artificial system of the (metallic) spatial network structure and the natural bone is basically replicated.

The femur element and the tibia element can both assume known shapes, beginning from the shapes of a so-called slide endoprosthesis, wherein the complete collateral ligaments and the rear cruciate ligament must be intact, via that of the so-called sliding axis endoprosthesis (see German published patent application DE-A 25 49 819), in which a rear cruciate ligament is not a precondition for an implantation, but the collateral ligaments are still intact, and furthermore by the shape of a so-called cone endoprosthesis (DE-A 39 22 294), in which, in comparison with the sliding axis endoprosthesis, the collateral ligaments need only be moderately intact, up to the shape of the so-called pole endoprosthesis (DE-A 41 41 757), in which all ligaments are dispensed with.

The ideal standard with regard to a minimal resection is completely met with the endoprosthesis of the invention. Should a revision intervention nonetheless occur, the femur element and the tibia element can be easily separated by a blade saw, which simply needs to be guided between the tibia element or the femur element and the support or joint surface, in order to cut through the bone trabeculae formed there and remove the endoprosthesis elements. Thereafter, there still exists the possibility of providing the patient with a conventional shank endoprosthesis, if the shankless endoprosthesis of the invention can no longer be taken into consideration for a renewed implantation. Here, it is possible to fall back on the same type of artificial knee joint.

If thus, for example, an endoprosthesis of the invention is first of all implanted in the form of a sliding axis endoprosthesis, but complications nevertheless occur later, then it is possible (presupposing the same ligament picture) to implant a shank endoprosthesis in the configuration of a sliding axis endoprosthesis. The same applies for all other prosthesis types mentioned.

Consequently, the endoprosthesis of the invention accomplishes not only the above-mentioned object. Rather, it also offers a type of modularity and many-sidedness with respect to possible revision interventions, as was not known up until now.

Further advantageous embodiments are indicated in the dependent claims.

In accordance with a first advantageous embodiment, it is provided that a centering pin pointing toward the tibia is formed on the tibia element. This pin has nothing in common with a conventional shank. Rather, it only projects a few centimeters to millimeters from the horizontal resection surface of the tibia into the interior of the bone, in order to effect there the centering of the tibia element. It is namely of great importance that the tibia element sits absolutely centered on the tibia end.

In accordance with a still further advantageous embodiment, it is provided that an antirotation shield running from medial to lateral toward the tibia is provided on the tibia element. This shield pushes into the spongiosa of the tibia bone and offers an absolute rotational stability of the tibia element on the tibia.

Preferably, the mentioned centering pin (to the extent that it is present) is covered with a three-dimensional open-mesh spatial network structure, into which once again bone trabeculae can grow, and thus provides for a durable connection of the pin with the bone as well.

Preferably, it is provided that the angle between the latches angled on the tibia element and the latches angled on the femur element in relation to the respective horizontal lies in the range between 15 and 75°. An angle of 45° is especially preferred, since a balanced proportion between the horizontal and vertical components of the introduced compressive force thereby exists.

In no case should the mesh width of the open-mesh spatial network structure be smaller than 500 $\mu$m, since otherwise the growth of the bone into the structure and through it would turn out to be too small for it to be able to exert the intended function of accommodating and transmitting all forces, during the shifting of burden as well. Bone material which would grow on a surface structure with a mesh width of below 500 $\mu$m would, in contrast, only be capable of bearing a load to a limited extent, and the purpose intended within the framework of the present invention could not be attained.

With diagnoses in which the two lateral ligaments as well as the rear cruciate ligament are still largely intact, non-physiological sequences of motion can nonetheless take place owing to the forces introduced through the ligaments.

This effect is counteracted (thus the sequence of motion is modeled more physiologically) by a refinement of the invention in which the glide tracks of the tibia element are embodied in a plastic bearing, which is pivotable or rotatable about an angle $\alpha$ in the $\alpha<\pm20°$ range about the equilibrium position.

Thus, proceeding from the usual configurations of a tibia element of an artificial knee joint, in which namely a plastic bearing is rigidly connected with the remaining tibia element (usually of metal), with this embodiment the bearing is maintained pivotable about the pin mentioned above. Preferably, the pin, around which the plastic bearing is pivotable, sits approximately centrally in the middle part of the tibia element. The main axis of the pin runs from caudal to cranial.

This refinement offers the possibility that the plateau or the plastic bearing can execute offsetting motions, if perhaps the ligament forces are non-symmetrical upon a bending motion of the artificial knee joint. In this case, the plateau with its sliding tracks pivots in the appropriate direction, so that the artificial condyles of the femur element can slide and roll away on the sliding tracks, imitating the physiological motion of the natural knee joint.

According to a still further preferred refinement of the embodiment previously mentioned, the swivel range of the plastic bearing is limited by an edge running at least partly around the periphery of the bearing surface of the tibia element, enclosing the plastic bearing with play and acting as buffer for this.

This construction provides a high safety in relation to an uncontrolled rotation of the plastic bearing, even under extreme conditions or stresses.

The invention will now be explained by way of example on the basis of two embodiments.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings.

In the following, like elements are provided with the same reference numerals.

DETAILED DESCRIPTION OF THE INVENTION

Figure 1:
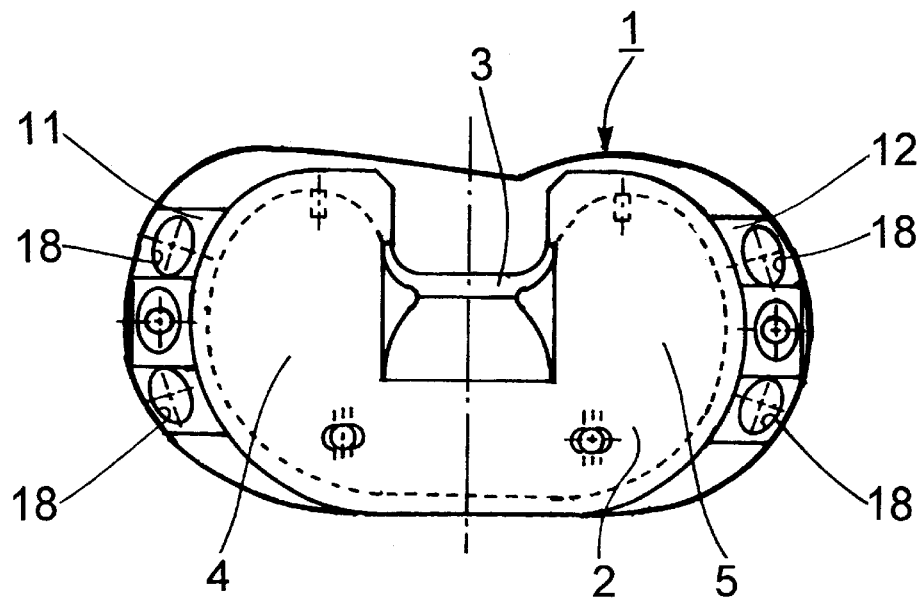
FIG. 1 is the front end view of a tibia element of the knee joint endoprosthesis configured as a slide endoprosthesis.

FIG. 1 shows the tibia element 1 in front end view. The inlet 2 has the guide bar 3 in the middle, which is constructed between slide tracks 4 and 5.

Figure 2:
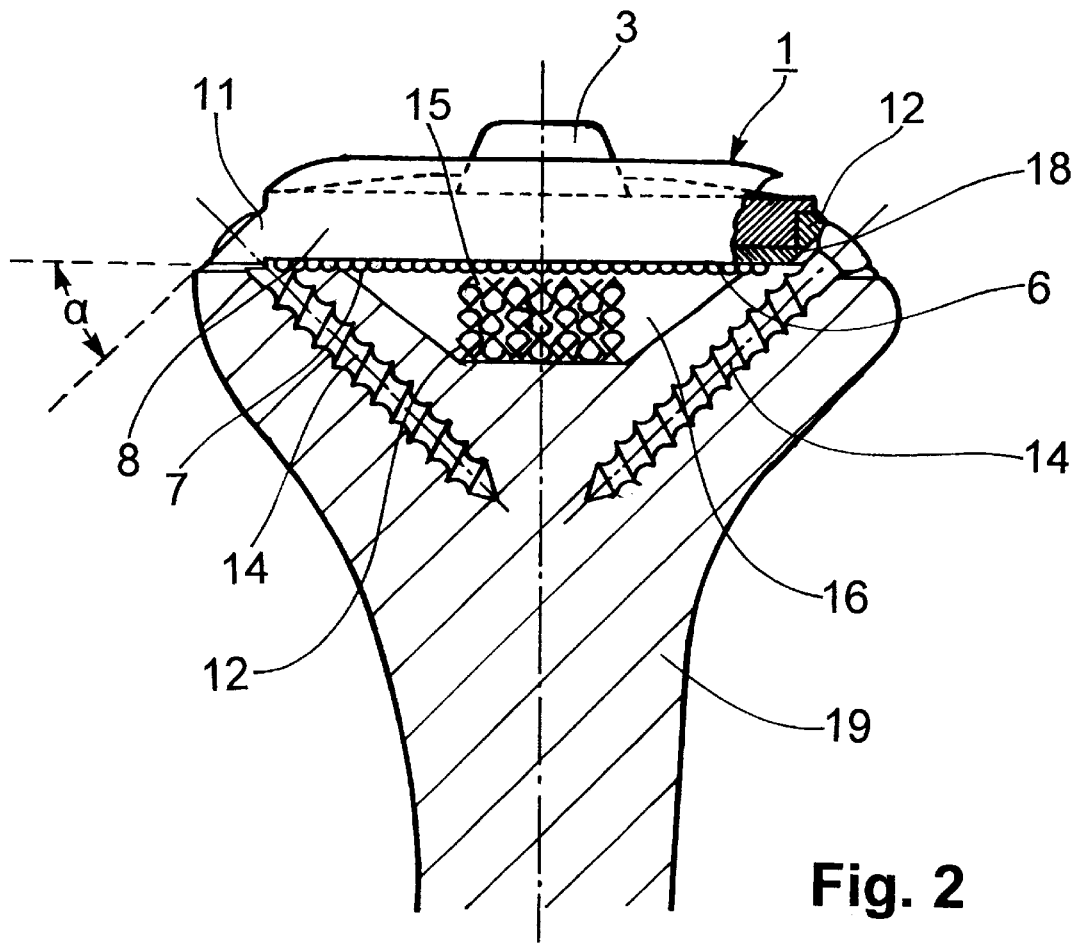
FIG. 2 is a lateral-medial section through the tibia element in accordance with FIG. 1 and a suggested tibia bone.

The tibia element 1 has a horizontal support surface 6 (FIG. 2), which comes to lie flat on the resected tibia surface. The resection surfaces on the tibia 19, as well as on the femur 29, are preferably produced with the aid of the nailing and resection theories according to DE 197 16 300 as well as DE-A-44 23 717.

The horizontal support surface 6 of the tibia element 1 is provided with an open-mesh, three-dimensional spatial network structure 7, into which and through which bone trabeculae are supposed to grow for secondary fixation of the tibia element 1 and the tibia 19. The spatial network structure 7 is an integral component of the base structure 8 of the tibia element 1. Preferably, the base structure 8 is produced together with the spatial network structure 7 in an investment casting process in a single operation. This guarantees the necessary stability of structure on base 8.

Respective latches 11 and 12 angled toward the tibia at an angle $\alpha$ to the horizontal are formed laterally or medially on the tibia element 1. The latches 11 and 12 are provided with at least one through hole 18, in the present case with at least three respective through holes. Through this through hole 18 a bone screw 14 can be inserted and screwed obliquely into the tibia bone corresponding to angle inclination a of latches 11 and 12. The desired tension of the tibia element 1 on tibia 19 is thereby generated. The diagonal tension generated leads to the spatial network structure 7 being pressed downward in FIG. 2, so that the underlying bone material is stimulated to sprout into the spatial network structure 7.

In the present case the tibia element 1 has another centering pin 15 fastened into the tibia 19, which here is likewise covered with a three-dimensional open-mesh spatial network structure 17.

The centering pin 15 provides for an optimal position of the tibia element 1 on the resected tibia stump. The optimal position is maintained stable in the present case by a formed-on antirotation shield 16, which runs from medial to lateral and encloses the centering pin 15.

Figure 4:
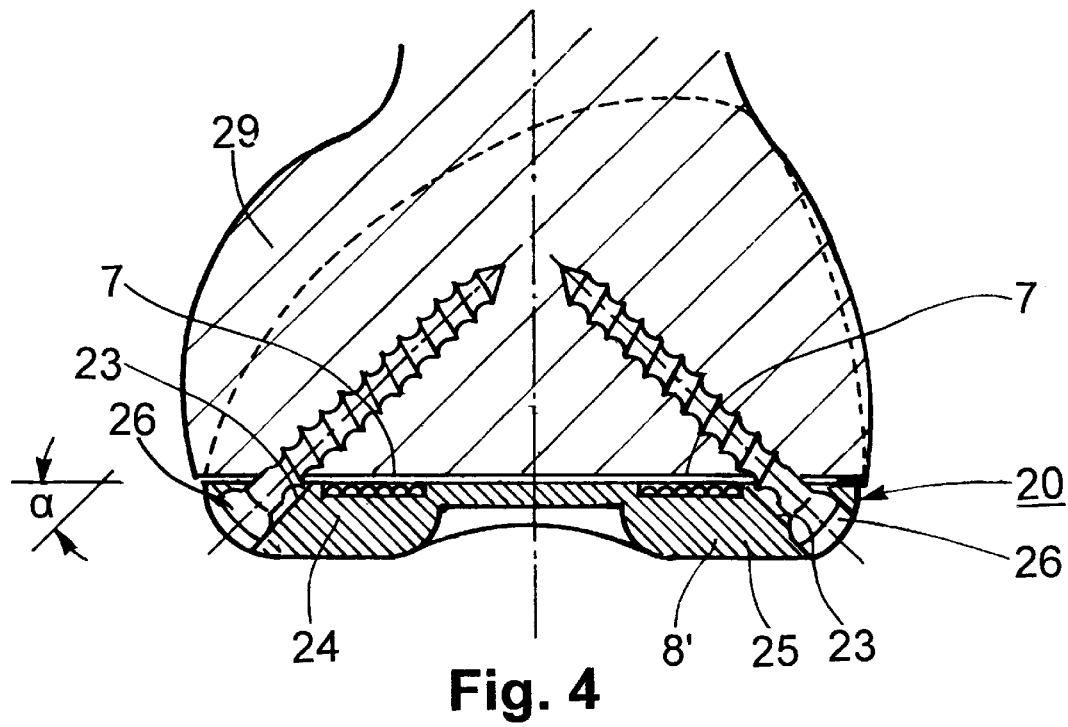
FIG. 4 is a sectional view along section line IV—IV of FIG. 3.
Figure 3:
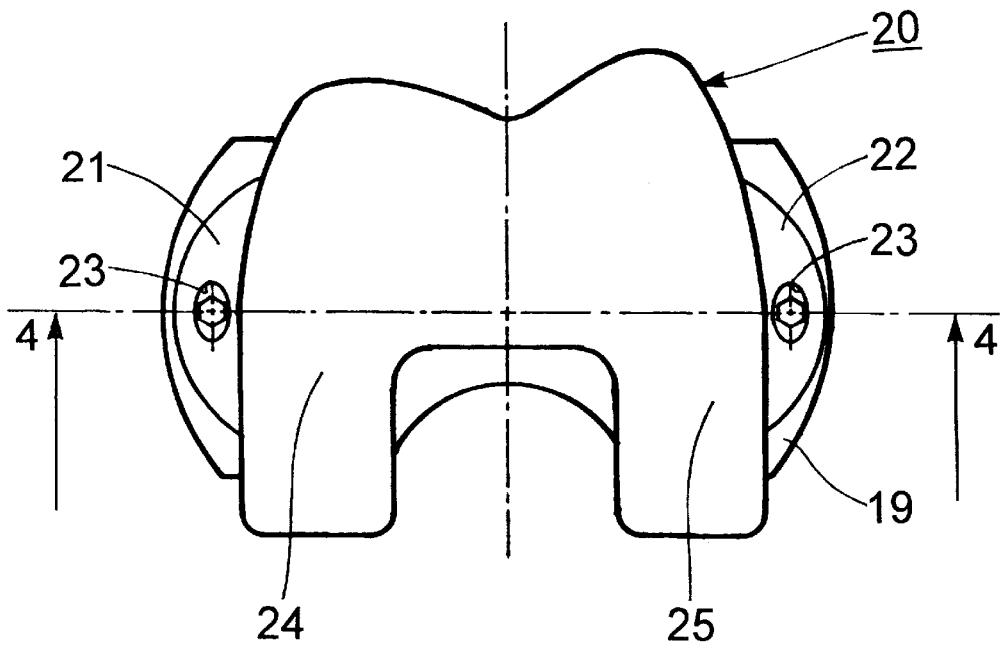
FIG. 3 is a front end view of the condyles of the femur element of the endoprosthesis configured as a slide endoprosthesis.
Figure 5:
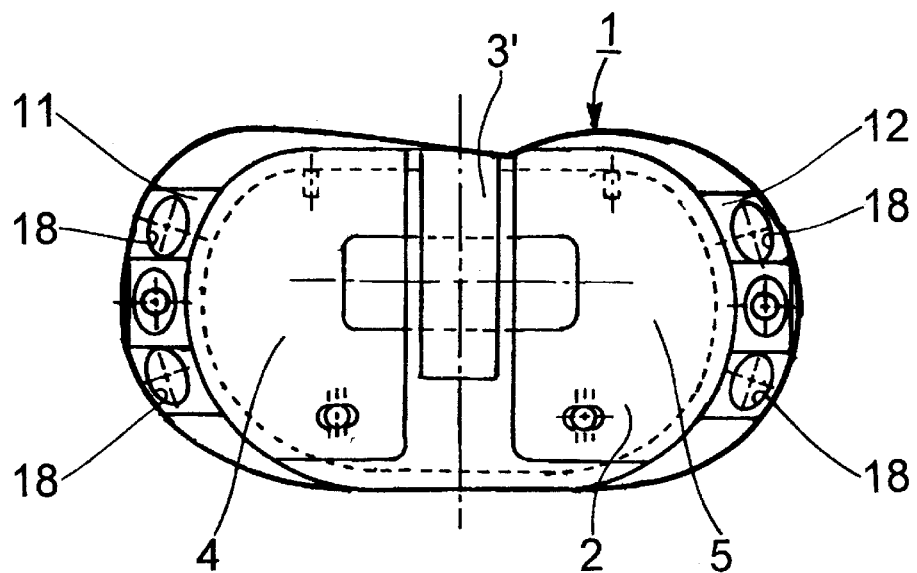
FIG. 5 is a front end view of the tibia element of the knee joint endoprosthesis configured as a sliding axis endoprosthesis.
Figure 6:
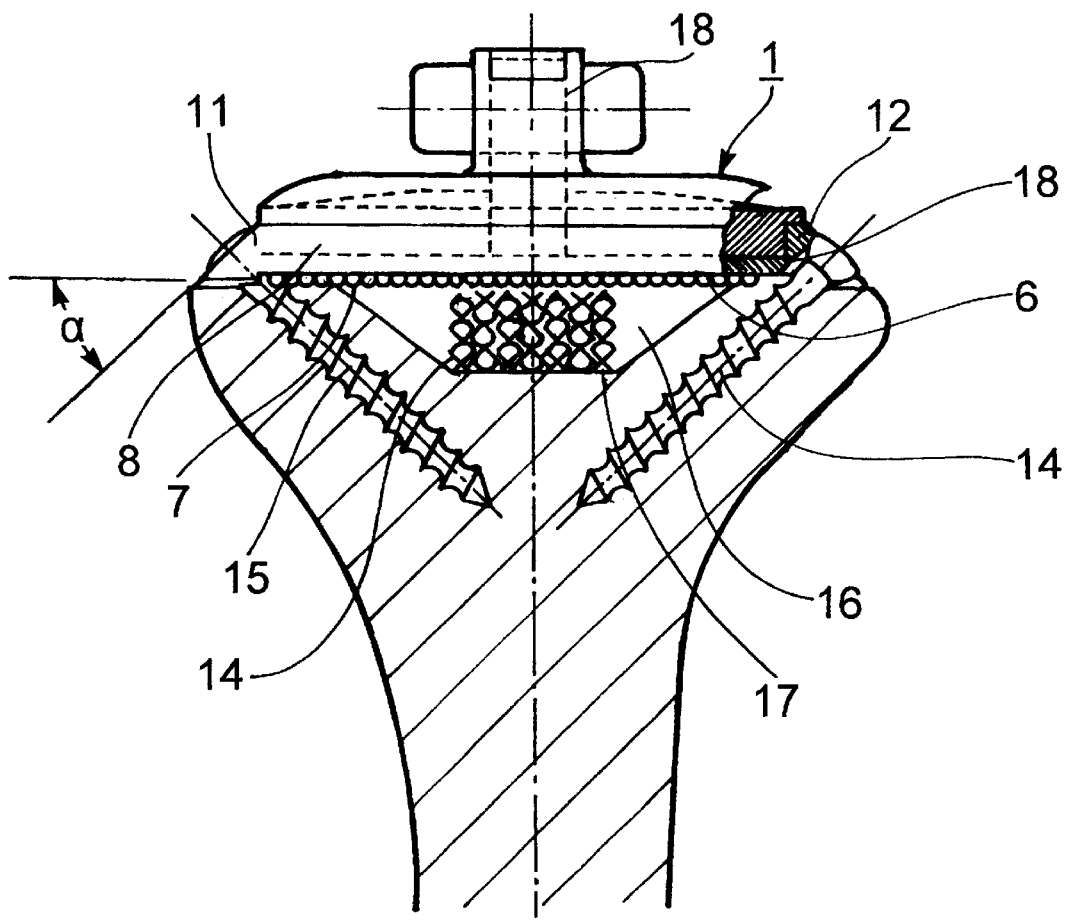
FIG. 6 is a sectional view from lateral to medial through the tibia element according to FIG. 5 and the tibia bone.
Figure 8:
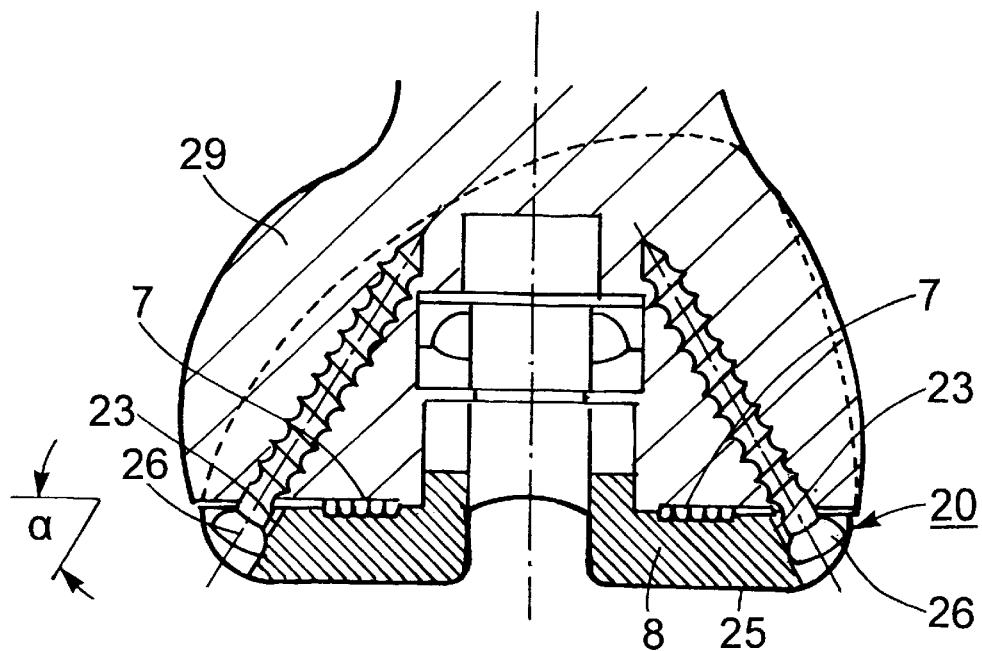
FIG. 8 is a sectional view along line VIII—VIII in FIG. 7.
Figure 7:
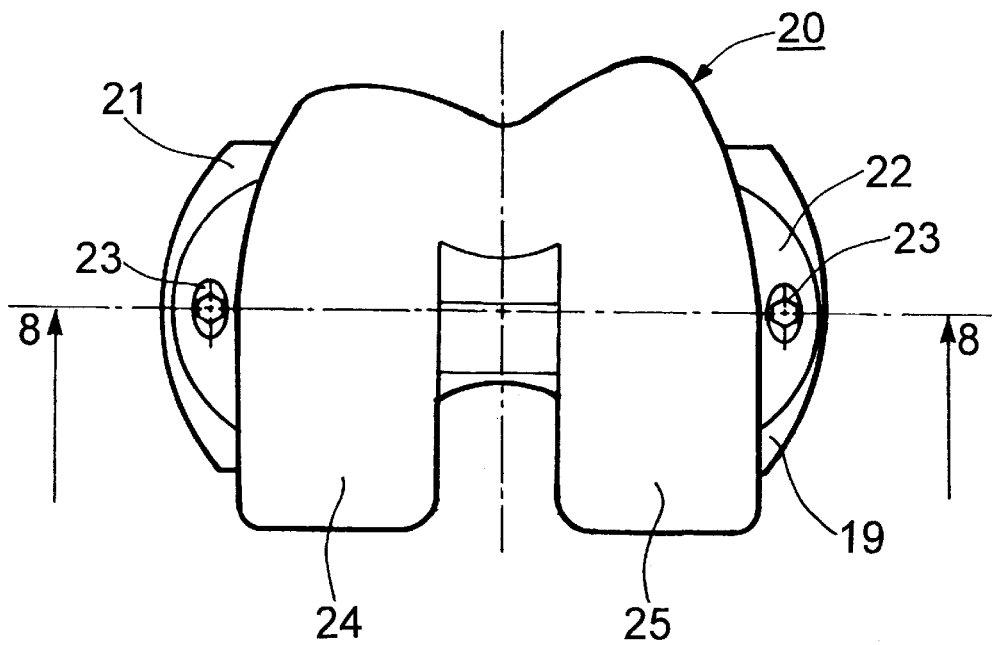
FIG. 7 is a front end view of the femur element of the knee joint endoprosthesis configured as a sliding axis endoprosthesis.

A femur element 20 can be gathered from FIG. 3, which forms a slide endoprosthesis with the tibia element 1 from FIG. 1. The femur element 20 has available two runners 24 and 25, imitating the natural condyles. Laterally and medially formed-on is respectively a latch 21, 22 with a through hole 23 angled toward the femur. The implantation position is evident from FIG. 4.

In the present case, only the horizontal joint surface of the femur element 20 is recognizable, and indeed as it is covered with the spatial network structure 7. The diagonal joint surfaces (not represented) are likewise covered with this spatial network structure 7.

A respective bone screw 26 is inserted through the through holes 23 and screwed into the bones of the femur 29. The angling of the latches 21 and 22 at an angle $\alpha$ to the horizontal provides (as already in the case of the tibia element 1) for a diagonal bracing of the femur element 20 on the femur bone 29 and therewith for a compression of the resection surfaces on the femur 29 by the femur element 20, owing to which once again the bone is stimulated to an amplified growth into and through the spatial network structure 7.

In order for the fusion of the femur element 20 with the femur bone 29 to be durable, the spatial network structure 7 is constructed as an integral component of the base structure 8' of the femur element 20.

FIGS. 5 through 8 depict a further embodiment of a knee joint prosthesis, and to be sure constructed as a sliding axis endoprosthesis, as emerges from DE 25 49 819, for example. These representations serve to illustrate the fact that the femur element 20 and the tibia element 1 can assume all known forms of knee joint endoprostheses. The system is thus extremely many-faceted. Differences from the embodiment according to FIGS. 1 through 4 exist with respect to the construction and the interplay between the femur element 20 and the tibia element 1. The features essential to the invention, however, are once more the angled side latches 11, 12 and 21, 22, as well as the spatial network structure 7 on the support surface(s).

Figure 9:
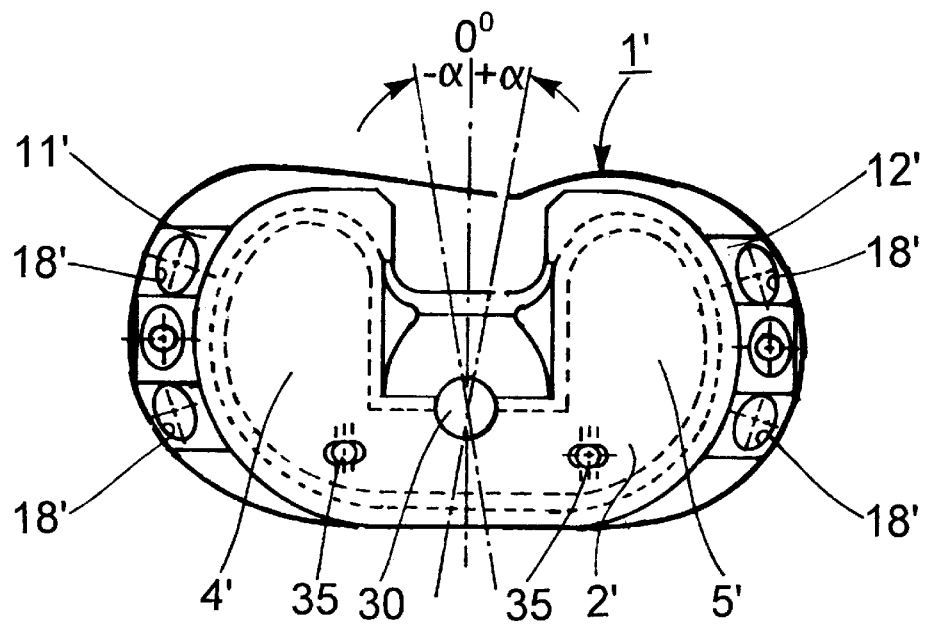
FIG. 9 is a front end view of a tibia element with pivotably mounted plastic support.
Figure 10:
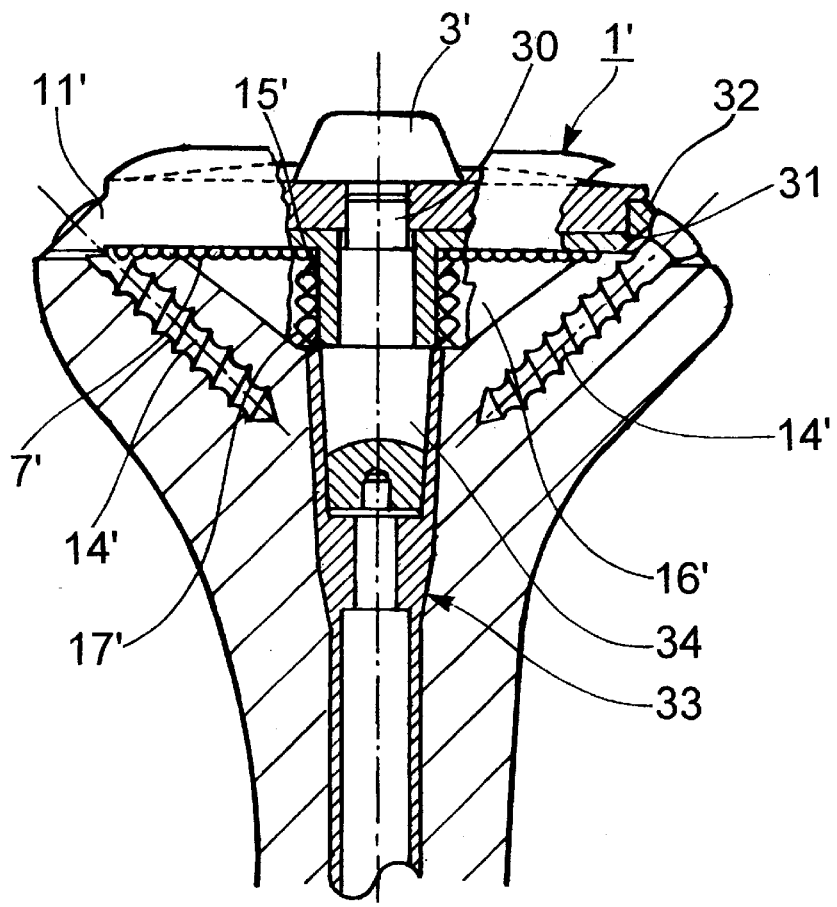
FIG. 10 is a lateral-medial section through the tibia element according to FIG. 9 and an indicated tibia bone.

FIGS. 9 and 10 show the preferred refinement of the endoprosthesis, which is used particularly with largely intact lateral ligaments as well as an intact cruciate ligament.

In the plastic support 2', the two sliding tracks 4' and 5' are formed. In the center of the plastic support 2' this is pivotable around a pin 30 set in tibia element 1' (see FIG. 10), and to be sure about an angle α in the range between −20 and +20° viewed from the central equilibrium point. Offset motions of the plastic support 2' thereby become possible owing to asymmetrically acting forces in the largely intact lateral ligaments and rear cruciate ligament. The offset motion leads to the condyles of the femur element being able always to roll away on a maximal slide and roll away surface. An almost optimal physiological sequence of motions is hereby made possible.

The pivot range of the plastic support 2' in the present case (FIG. 10) is restricted by an edge 32 at least partially running around on the periphery of the support surface 31 of the tibia element 1'. The edge 32 encloses the plastic support 2' with play and acts as a buffer for it. Among other things, the amount of the play in the final analysis defines the pivot range of the plastic support 2'.

Through holes 35 in the plastic support 2' permit flushing of the entire joint with the joint fluid, the so-called synovial fluid.

Moreover, it is furthermore provided in the embodiment according to FIG. 10 that on the centering pin 15' formed-on toward the tibia a central guide element 33 is couplable by means of a conical clamping 34. In the present case, the guide element 33 is represented as an extension shank. It should basically be stressed in this connection that the guide element 33 does not act like a conventional shank endoprosthesis.

It will be appreciated by those skilled in the art that changes could be made to the embodiment(s) described above without departing from the broad inventive concept thereof. It is understood, therefore, that this invention is not limited to the particular embodiment(s) disclosed, but it is intended to cover modifications within the spirit and scope of the present invention as defined by the appended claims.

We claim:

1. A knee joint endoprosthesis comprising:
   a substantially U-shaped femur element (20), viewed from medial to lateral, having a horizontal, two diagonal and two vertical joint surfaces facing a femur for installation on a resected femur bone (29), the femur element (20) being provided with two runners (24, 25), and
   a tibia element (1) having two slide tracks (4, 5) on which the runners (24, 25) of the femur element (20) execute a rolling away and optionally a sliding motion, the tibia element (1) having a horizontal support surface (6) facing a tibia for supporting a resected tibia (19),
   wherein the femur element (20) and the tibia element (1) are constructed shanklessly,
   at least the horizontal and both diagonal joint surfaces of the femur element (20) and the horizontal support surface (6) of the tibia element (1) are provided with an open-mesh, three-dimensional spatial network structure (7), which is an integral component of a base structure (8, 8') of the femur element (20) and the tibia element (1),
   medially and laterally on the femur element (20), two latches (21, 22) angled toward the femur are formed-on with respectively at least one through hole (23) into which a respective bone screw (26) can be inserted, and
   medially and laterally on the tibia element (1), two latches (11, 12) angled toward the tibia are formed-on with respectively at least one through hole (18) into which a respective bone screw (14) can be inserted.

2. The knee joint endoprosthesis according to claim 1, wherein a centering pin (15) is formed on the tibia element (1) facing the tibia.

3. The knee joint endoprosthesis according to claim 1, wherein an antirotation shield (16) running toward the tibia from medial to lateral is provided on the tibia element (1).

4. The knee joint endoprosthesis according to claim 2, wherein the centering pin (15) has a three-dimensional open-mesh spatial network structure (17).

5. The knee joint endoprosthesis according to claim 1, wherein the angle α between the latches (11, 12; 21, 22), angled on the tibia element (1) and on the femur element (20), and the horizontal lies in a range from $15° < α < 75°$.

6. The knee joint endoprosthesis according to claim 5, wherein the angle $α = 45°$.

7. The knee joint endoprosthesis according to claim 1, wherein the mesh width of the open-mesh spatial network structure (7) amounts to a minimum of 500 µm.

8. The knee joint endoprosthesis according to claim 1, wherein the slide tracks (4', 5') of the tibia element (1') are formed in a plastic support (2') which is pivotable around a pin (30) set into the tibia element (1'), the plastic support (2') being pivotable about an angle α in a swivel range $α < ±20°$ around an equilibrium position.

9. The knee joint endoprosthesis according to claim 8, wherein the swivel range of the plastic support (2') is restricted by an edge (32) at least partially running around on a periphery of a support surface (31) of the tibia element (1'), enclosing the plastic support (2') with play, and acting as a buffer.

* * * * *